(12) United States Patent
Weckbecker et al.

(10) Patent No.: US 6,291,710 B1
(45) Date of Patent: Sep. 18, 2001

(54) PROCESS FOR PREPARING SULFONYL HALIDES

(75) Inventors: Christoph Weckbecker, Gründau; Erich Kraus, Offenbach; Karlheinz Drauz, Freigericht, all of (DE)

(73) Assignee: Degussa AG, Frankfurt am Main (DE)

( * ) Notice: Subject to any disclaimer, the term of this patent is extended or adjusted under 35 U.S.C. 154(b) by 0 days.

(21) Appl. No.: 09/382,781

(22) Filed: Aug. 25, 1999

(30) Foreign Application Priority Data

Aug. 25, 1998 (DE) .............................................. 198 36 516

(51) Int. Cl.$^7$ ....................................................... C07F 9/02
(52) U.S. Cl. .............................................................. 562/828
(58) Field of Search ............................................... 562/828

(56) References Cited

U.S. PATENT DOCUMENTS 3,755,430 * 8/1973 Lorenz et al. .
4,215,071 * 7/1980 Blank .

FOREIGN PATENT DOCUMENTS

| 414426 C | 5/1925 | (DE) . |
| 1200809 B | 9/1965 | (DE) . |
| 2240883 | 2/1974 | (DE) . |
| 19732030 A | 1/1999 | (DE) . |

OTHER PUBLICATIONS

Troyanski et al., "Rearrangement of Sulphonamidyl Radicals With Hydrogen Migration", Bulletin of the Academy of Sciences of the USSR, Division of Chemical Science, Bd. 35, No. 7, pp. 1428–1434 (Jul. 1986), Abstract XP002122900.

King et al., "Mechanisms of Hydrolysis and Related Nucleophilic Displacement Reactions of Alkanesulphonyl Cholorides: pH Dependence and the Mechanism of Hydration of Sulphenes", Journal of the American Chemical Society, Bd. 114, No. 5 (Feb. 1992), pp. 1743–1749, Abstract XP002122901.

Kotoris et al., "Novel Phosphate Mimetics for the Design of Non–peptidyl Inhibitors of Protein Tyrosine Phosphatases", Bioorganic and Medicinal Chemistry Letters, Bd. 8, No. 22 (Nov. 1998), pp. 3275–3280, Abstract XP004143741.

* cited by examiner

Primary Examiner—Paul J. Killos
(74) Attorney, Agent, or Firm—Pillsbury Winthrop LLP

(57) ABSTRACT

A process for preparing compounds of the general formula (I)

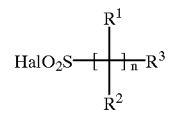

from compounds of the general formula (II)

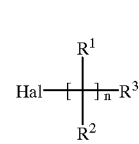

and sulfite salts with subsequent halogenation. The solvent which is used for halogenation is an organic solvent which is fully or partly miscible with water. The sulfonyl halides are useful for synthesizing bio active substances.

14 Claims, No Drawings

PROCESS FOR PREPARING SULFONYL HALIDES

CROSS-REFERENCE TO RELATED APPLICATION

This application is based on German Application DE 198 38 516.1, filed Aug. 25, 1998, which disclosure is incorporated herein by reference.

FIELD OF THE INVENTION

The present invention relates to a process for preparing compounds of the general formula (I)

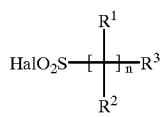

in which
n=1 to 18,
$R^1$, $R^2$, independently, represent H, F, Cl, Br, ($C_1$–$C_8$)-alkyl, ($C_1$–$C_8$)-alkoxy, ($C_2$–$C_8$)-alkoxyalkyl, ($C_3$–$C_8$)-cycloalkyl, ($C_6$–$C_{18}$)-aryl, ($C_7$–$C_{19}$)-aralkyl, ($C_3$–$C_{18}$)-heteroaryl, ($C_4$–$C_{19}$)-heteroaralkyl, ($C_1$–$C_8$)-alkyl-($C_6$–$C_{18}$)-aryl, ($C_1$–$C_8$)-alkyl- ($C_6$–$C_{18}$)-heteroaryl, ($C_1$–$C_8$)-alkyl-($C_3$–$C_8$)-cycloalkyl or ($C_3$–$C_8$)-cycloalkyl-($C_1$–$C_8$)-alkyl group, or $R^1$ and $R^2$ are linked via a ($C_3$–$C_7$)-carbocyclic compound for the same values of n,
with the proviso that $R^1$ and $R^2$ may each be regarded per se as representing different substituents,
$R^3$ represents H, Cl, Br, I or $R^1$,
Hal represents Cl or Br,
from compounds of the general formula (II)

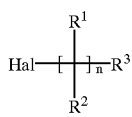

in which
n, $R^1$, $R^2$, $R^3$ and Hal are defined in the same way as set forth above, and sulfite salts with subsequent halogenation. The invention also provides use of compounds of the general formula (I).

Compounds of the general formula (I) are important substrates for the synthesis of bioactive substances such as, for example, the fungicide Methasulfocarb® (CAS-No.: 66952-49-6).

BACKGROUND OF THE INVENTION

DE 1200809 describes two ways to prepare chloromethanesulfonic acid chloride. Both use s-trithian as starting material and produce yields of only 51.6% and 61.7%. In addition, the relatively expensive starting material, s-trithian is also required to prepare the desired derivatives. Also, pure products are not obtained by this process. Rather, mixtures of mono- and polychloroalkylsulfonic acid chlorides are produced, which are difficult to separate completely. Also a number of sulfur-containing side products are produced, the waste disposal of which can cause problems.

DE-OS 2545644 discloses a process by which R-Hal compounds are reacted with sulfite salts by phase transfer catalysis in water to give salts of sulfonic acids. In a separate second step, after isolation and drying, the sulfonic acid salts obtained are converted into the corresponding sulfonic acid chlorides by means of a chlorinating agent. Yields of 69% are achieved. In this process, production of the sulfonic acid and chlorination are separated by a drying stage. The disadvantage is that the salt mixture which is used for chlorination has to be extremely dry (s. Organikum 1986, 16th edition VEB, bottom cf p. 422), since residues of the aqueous solvent from the first step lead to a higher consumption of the chlorinating agent and to an increase in the range of secondary products.

This extreme drying of salt mixtures, however, is very difficult to achieve in an industrial process and leads to a time-consuming, cost-intensive drying procedure. Also, the handling of solids is an obstacle to industrial use of the process.

SUMMARY OF THE INVENTION

The object of the invention, therefore, was to provide a process which enabled the preparation of sulfonic acid halides in improved yields while avoiding intermediate isolation and drying of the sulfonic acid salts.

Accordingly compounds of the general formula (I)

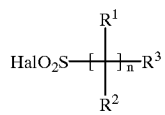

in which
n=1 to 18,
$R^1$, $R^2$, independently, represent, H, F, Cl, Br, ($C_1$–$C_8$)-alkyl, ($C_1$–$C_8$)-alkoxy, ($C_2$–$C_8$)-alkoxyalkyl, ($C_3$–$C_8$)-cycloalkyl, ($C_6$–$C_{18}$)-aryl, ($C_7$–$C_{19}$)-aralkyl, ($C_3$–$C_{18}$)-heteroaryl, ($C_4$–$C_{19}$)-heteroaralkyl, ($C_1$–$C_8$)-alkyl-($C_6$–$C_{18}$)-aryl, ($C_1$–$C_8$)-alkyl-($C_6$–$C_{18}$)-heteroaryl, ($C_1$–$C_8$)-alkyl-($C_3$–$C_8$)-cycloalkyl or ($C_3$–$C_8$)-cycloalkyl-($C_1$–$C_8$)-alkyl group, or $R^1$ and $R^2$ are linked via a ($C_3$–$C_7$)-carbocyclic compound for the same values cf n,
with the proviso that $R^1$ and $R^2$ may each be regarded per se as representing different substituents,
$R^3$ represents H, Cl, Br, I or $R^1$,
Hal represents Cl or Br,
are prepared from compounds of the general formula (II)

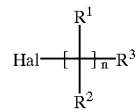

in which
n, $R^1$, $R^2$, $R^3$ and Hal are defined in the way given above,
and sulfite salts with subsequent halogenation, wherein subsequent halogenation is performed in an organic solvent which is fully or partly miscible with water, so that high purity compounds of the desired type are obtained in very good yields, dissolved in the organic solvent but, without intermediate isolation of a solid, apart from the salts.

In the context of the invention, compounds where n=1, $R^1$, $R^2$=H, Hal=Cl and $R^3$=H, Cl, Br, I or $R^1$ are preferred. A compound in which n=1, $R^1$, $R^2$=H, Hal=Cl and $R^3$=Cl is particularly preferably prepared by the process according to the invention.

Reaction of the sulfite salt with the compound of the general formula II, in which n, $R^1$, $R^2$, $R^3$ and Hal may be defined in the same way as above, is preferably performed in water as solvent. Optionally, water-miscible organic solvents such as, for example, alcohols such as methanol or ethanol etc., or ethers such as tetrahydrofuran (THF) or dioxan, or ketones such as acetone, may also be admixed with the water. Phase transfer catalysis, as described in DE 2545644, may also be suitable here.

In principle any organic solvent which is either fully or partly miscible with water and is familiar to a person skilled in the art is suitable as long as it enables the water to be removed from the reaction mixture. Ternary mixtures with water as one component are also suitable for this purpose. However, the use of ethers during subsequent halogenation is preferred. Particularly preferred ethers which may be mentioned are diethylene glycol dimethyl ether, triethylene glycol dimethyl ether, tetraethylene glycol dimethyl ether, diethylene glycol diethyl ether, triethylene glycol diethyl ether or tetraethylene glycol diethyl ether.

Any salts familiar to a person skilled in the art and known to be used for this purpose are suitable as sulfite salts (Houben-Weyl, Methoden der Organischen Chemie vol. 9, p. 347 et seq. or E11, p. 1055). However, the use of alkali metal or alkaline earth metal sulfite salts or ammonium sulfite salts and their hydrogen sulfite salts is preferred. Sodium sulfite is particularly preferably used.

A number of halogenating agents which can be used are described in Houben-Weyl (Methoden der organischen Chemie E11, p. 1071 et seq. or VIII p. 347 et seq.). The following may preferably be used: thionyl chloride, phosphorus pentachloride, phosphorus trichloride, phosphorus oxychloride, oxalyl chloride. However, the use of phosgene as halogenating agent is particularly preferred.

As described above, preparation of the sulfonic acid salt is preferably performed in aqueous media. The temperature during reaction may vary between 20° and 200° C., preferably between 40° and 150° C. The reaction is preferably performed in a sealed vessel. The pressure, which may be adjusted during reaction, is generally between 1 and 100 bar, preferably 3 to 15 bar.

Subsequent halogenation may be performed at a temperature of 0° to 150° C., preferably 50° to 100° C.

A catalyst is preferably used when halogenating with phosgene. These types of catalysts are, inter alia, N-alkyllactams, such as N-methylpyrrolidone, and the compounds mentioned in DE 2743542 and the references cited there. The use of DMF for this purpose is particularly preferred.

The invention also provides use of the compounds of the general formula (I) prepared by the process in claim 1 in syntheses for preparing bioactive substances.

The reaction of sulfite salts with organic halides is particularly preferably performed in water as solvent. In this case, e.g. sodium sulfide is dissolved in water and optionally an alcohol or acetone (phase-facilitator) and e.g. a haloalkane such as methylene chloride are added. The use of a phase-facilitator during reaction, however, is not absolutely necessary. The reaction proceeds without any problems with a yield of 88 to 91%.

As indicated above, subsequent halogenation, for example chlorination, has to be performed under anhydrous conditions. A number of possibilities are available to a person skilled in the art. Inter alia, the concentrated aqueous product phase can be dewatered azeotropically with a non-water-miscible solvent. In this case, however, the salt formed in the preliminary stage precipitates out and this leads to caking and incrustations in the reactor and on the agitator which prevents industrial use of this variant. The disadvantage of extreme drying of a salt mixture has already been described above.

According to the invention, therefore, the aqueous product phase from sulfonate production is converted in an organic solvent by adding a partially or fully water-miscible organic solvent, whereupon water can readily be removed by distillation from the reaction mixture with the aid of this.

This is preferably achieved by using the high-boiling ethers mentioned above.

In particular, diethylene glycol dimethyl ether was tested for suitability. The sulfonate solution was highly concentrated, diethylene glycol dimethyl ether was added and the water was removed by distillation. In this process, only a liquid phase is ever present, in which the solid (salt) is homogeneously distributed. There is therefore no tendency for solid to collect at the reactor wall.

After the water has been removed from the reaction mixture by distillation, which is achieved in a technically simpler manner than concentrating a salt mixture to dryness, halogenation can take place. Phosgene is preferably used as the agent of choice for chlorination. The reaction may be catalysed, e.g. by N,N-dialkylformamides, preferably N,N-dimethylformamide. The optimum amount of catalyst is 0.1–20 mol. %, preferably 0.2–5 mol. %. Reaction starts in this specific case at a temperature of 40° C., but higher temperatures are more beneficial. Phosgene preferably reacts within a short time at 80° C. so that, with continuous addition, only low phosgene concentrations are reached in the reaction mixture.

Surprisingly, it was observed that halogenation of sulfonates with phosgene in ethers as solvent proceeded up to 10 times more rapidly than in, for example, toluene or when halogenating solid salt mixtures.

After the completion of halogenation, filtration of the salts and, in the case of chloromethanesulfonic acid chloride preparation, distillative woiking-up of the product is performed, wherein this is distilled off at 72° C./20 mbar and the high-boiling ether used as solvent remains behind in the liquid phase. The product obtained in this way has an outstanding purity of >98% after separation from the solvent.

Alternatively, the product may also be distilled out of the reaction mixture first, after the halogenation step, as described above and then the salts may be filtered off.

In any case, the solvent used may be used again in the following reaction in the form in which it is then present, or, preferably, it may first be purified by distillation.

Surprisingly, the choice of a suitable solvent for halogenation is. the reason why an advantageous one-pot process can be used on an industrial scale for the synthesis of sulfonic acid halides, without intermediate isolation of the intermediates. This had not been expected from the beginning and is nonetheless of particular advantage from an economic point of view.

In the context of the invention, a $(C_1-C_8)$-alkyl group is understood to be a group with 1 to 8 saturated carbon atoms and may be branched in any way. The following groups in particular are included within this definition: methyl, ethyl, n-propyl, isopropyl, n-butyl, isobutyl, secbutyl, tert-butyl, pentyl, hexyl etc.

In the context of the invention, a $(C_1-C_8)$-alkoxy group is understood to be a group with 1 to 8 saturated carbon atoms which may be branched in any way and is linked to the molecule concerned via an oxygen atom. The following groups in particular are included within this definition: methoxy, ethoxy, n-propoxy, isopropoxy, n-butoxy, isobutoxy, sec-butxoy, tert-butoxy, pentoxy, hexoxy etc.

In the context of the invention a $(C_2-C_8)$-alkoxyalkyl group is a group with 2 to 8 saturated carbon atoms which may be branched in any way and in which one $CH_2$ unit in the group has been exchanged for an oxygen atom. The structure of the alkyl part of this group may have the form given for the alkyl groups mentioned above.

Similarly, in the context of the invention, a $(C_3-C_8)$-cycloalkyl group is a group from the set of cyclic alkyl groups with 3 to 8 carbon atoms and may optionally be branched in any way. The groups cyclopropyl, cyclobutyl, cyclopentyl, cyclohexyl, cycloheptyl are included in particular within this set. One or more double bonds may be present in this group.

A $(C_6-C_{18})$-aryl group is understood to be an aromatic group with 6 to 18 carbon atoms. This includes in particular compounds such as phenyl, naphthyl, anthryl, phenanthryl or biphenyl.

A $(C_7-C_{19})$-aralkyl group is a $(C_6-C_{18})$-aryl group bonded to the molecule via a $(C_1-C_8)$-alkyl group.

In the context of the invention, a $(C_3-C_{18})$-heteroaryl group is a live, six or seven-membered aromatic ring system consisting of 3 to 18 carbon atoms which (contains heteroatoms such as, for example, nitrogen, oxygen or sulfur, in the ring. The following groups in particular are regarded as being this type of heteroaromatic species: 1-, 2-, 3-furyl, or 1-, 2-, 3-pyrrolyl, 1-,2-,3-thienyl, 2-, 3-, 4-pyridyl, 2-, 3-, 4-, 5-, 6-, 7-indolyl, 3-, 4-, 5-pyrazole, 2-,4-, 5-imidazole, acridinyl, quinolinyl, phenanthridinyl, 2-, 4-, 5-, 6-pyrimidinyl.

A $(C_4-C_{19})$-heteroaralkyl group is understood to be a heteroaromatic system corresponding to the $(C_7-C_{19})$-aralkyl group.

DETAILED DESCRIPTION OF THE PREFERRED EMBODIMENTS

EXAMPLES

Example 1
Method of operation for synthesizing sodium chloromethanesulfonate Starting materials for 1 mol:
125.0 g (1 mol) sodium sulfite
1346 ml water
242.8 g (2.9 mol) methylene chloride 1346 ml of water are initially introduced and 1 mol of sodium sulfite is dissolved therein. Then methylene chloride is allowed to run in, with stirring, from a storage reservoir. The mixture is heated to 80° C. in a sealed reactor. The pressure equilibrates to about 4 bar and remains constant for the 7 h reaction time.

Example 2
Converting the sodium chloromethanesulfonate from Example 1 in a glycol ether without intermediate isolation and chlorination with phosgene Starting materials:
152.55 g (1 mol) sodium chloromethanesulfonate as an aqueous solution from Example 1.

600 ml diethylene glycol dimethyl ether
3.6 g (0.05 mol) N,N-dimethylformamide
128.5 g (1.3 mol) phosgene The aqueous solution from Example 1 is first concentrated by evaporation to a concentration of 70–80%, the temperature in the liquid phase being 120 to 124° C. After cooling to about 100° C. the glycol ether is added. The water present in the suspension is removed by distillation Chlorination:

After cooling the suspension to about 80° C., N,N-dimethylfornamide, as catalyst, is added and phosgene is introduced into the suspension as a liquid over the course of one hour. After 30 minutes of post-reaction time at 80° C. the suspension is cocled and the sodium chloride is filtered off. The product solution is distilled under vacuum.

Yield: 84–88% of chloromethanesulfonylchloride, with respect to sodium chloromethanesulfonate (B.pt. 72° C./20 mbar).

Overall yield: 74–80% of theoretical.

What is claimed is:

1. A one-pot process for preparing compounds of the general formula (I)

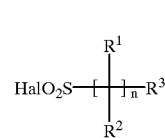

in which
n=1 to 18,
$R^1$, $R^2$, independently, represent H, F, Cl, Br, $(C_1-C_8)$-alkyl, $(C_1-C_8)$-alkoxy, $(C_2-C_8)$-alkoxyalkyl,$(C_3-C_8)$-cycloalkyl, $(C_6-C_{18})$-aryl, $(C_7-C_{19})$-aralkyl, $(C_3-C_{18})$-heteroaryl, $(C_4-C_9)$-heteroaralkyl, $(C_1-C_8)$-alkyl-$(C_6-C_{18})$-aryl, $(C_1-C_8)$-alkyl-$(C_6-C_{18})$-heteroaryl, $(C_1-C_8)$-alkyl-$(C_3-C_8)$-cycloalkyl or $(C_3-C_8)$-cycloalkyl-$(C_1-C_8)$-alkyl group, or $R^1$ and $R^2$ are linked via a $(C_3-C_7)$carbocyclic compound for the same value of n, with the proviso that $R^1$ and $R^2$ may each be regarded per se as representing different substituents,
$R^3$ represents H, Cl, Br, I or $R^1$,
Hal represents Cl or Br, by
reacting compounds of the general formula (II)

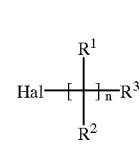

in which
n, $R^1$, $R^2$, $R^3$ and Hal maybe defined in the same way as set forth above,
with sulfite salts thereafter
halogenating with a halogenating agent in an organic solvent which is fully or partly miscible with water, and isolating compounds of general formula (I).

2. The process according to claim 1, wherein n=1, $R^1$, $R^2$=H, Hal=Cl and $R^3$ is defined in the same way as in claim 1.

3. The process according to claim 2, wherein n=1, $R^1$, $R^2$=H, $R^3$=Cl and Hal=Cl.

4. The process according to claim 1, wherein reaction of the sulfite salts with the compound of general formula II, in which n, $R^1$, $R^2$, $R^3$ and Hal are defined in the same way as set forth above, is performed in water as solvent.

5. The process according to claim 1, further comprising:
   halogenating in an ether which is fully or partly miscible with water as solvent.

6. The process according to claim 1, wherein the sulfite salts comprise sodium sulfite.

7. The process according to claim 1, wherein the halogenating agent comprises phosgene.

8. The process according to claim 1, further comprising: reacting the compound of formula (II) and the sulfite salts at a pressure of 1 to 100 bar.

9. The process according to claim 1, further comprising reacting the compound of formula (II) and the sulfite salts at a temperature of 20° to 200° C.

10. The process according to claim 9, wherein the temperature is 40° to 150° C.

11. The process according to claim 1, further comprising: halogenating at a temperature of >0° to 150° C.

12. The process according to claim 11 wherein the temperature is 50° to 100° C.

13. The process according to claim 1, further comprising: adding DMF as a catalyst during halogenation.

14. A process according to claim 8, wherein the pressure ranges from 3 to 15 bar.

* * * * *